(12) United States Patent
Lorio et al.

(10) Patent No.: US 9,883,955 B2
(45) Date of Patent: Feb. 6, 2018

(54) MINIMALLY INVASIVE INTERVERTEBRAL SYSTEMS AND METHODS

(71) Applicants: Morgan Packard Lorio, Bristol, TN (US); Thomas Purcell, Del Mar, CA (US)

(72) Inventors: Morgan Packard Lorio, Bristol, TN (US); Thomas Purcell, Del Mar, CA (US)

(73) Assignee: Morgan Packard Lorio, Bristol, TN (US)

( * ) Notice: Subject to any disclaimer, the term of this patent is extended or adjusted under 35 U.S.C. 154(b) by 0 days.

(21) Appl. No.: 15/175,032

(22) Filed: Jun. 6, 2016

(65) Prior Publication Data

US 2016/0302945 A1 Oct. 20, 2016

Related U.S. Application Data

(62) Division of application No. 13/248,747, filed on Sep. 29, 2011, now Pat. No. 9,358,131.

(Continued)

(51) Int. Cl.
*A61F 2/44* (2006.01)
*A61F 2/46* (2006.01)
(Continued)

(52) U.S. Cl.
CPC ............ *A61F 2/4611* (2013.01); *A61F 2/447* (2013.01); *A61F 2/4601* (2013.01); *A61F 2002/2835* (2013.01); *A61F 2002/305* (2013.01); *A61F 2002/3055* (2013.01); *A61F 2002/30143* (2013.01); *A61F 2002/30359* (2013.01); *A61F 2002/30382* (2013.01); *A61F 2002/30448* (2013.01); *A61F 2002/30462* (2013.01); *A61F 2002/30471* (2013.01); *A61F 2002/30502* (2013.01); *A61F 2002/30504* (2013.01); *A61F 2002/30522* (2013.01); *A61F 2002/30545* (2013.01); *A61F 2002/30556* (2013.01); *A61F 2002/30579* (2013.01); *A61F 2002/30598* (2013.01); *A61F 2002/30774* (2013.01); *A61F 2002/30828* (2013.01); *A61F 2002/4415* (2013.01); *A61F 2002/4475* (2013.01);

(Continued)

(58) Field of Classification Search
CPC combination set(s) only.
See application file for complete search history.

(56) References Cited

U.S. PATENT DOCUMENTS 6,039,761 A * 3/2000 Li .................... A61B 17/70
  623/17.16
8,454,623 B2 * 6/2013 Patel .................. A61F 2/447
  606/99

(Continued)

*Primary Examiner* — Jan Christopher Merene
(74) *Attorney, Agent, or Firm* — Michael R. Shevlin

(57) ABSTRACT

A minimally invasive intervertebral implant includes a circuitous body defining a luminal axis extending longitudinally therethrough. The circuitous body includes proximal and distal ends oppositely disposed along a lateral axis of the circuitous body. Each of the proximal and distal ends includes an aperture disposed therethrough such that the circuitous body includes a first configuration wherein the proximal and distal ends are at a maximum separation and a second configuration wherein the proximal and distal ends are closer together than in the first configuration.

34 Claims, 9 Drawing Sheets

Related U.S. Application Data

(60) Provisional application No. 61/389,986, filed on Oct. 5, 2010.

(51) Int. Cl.
    *A61F 2/28*     (2006.01)
    *A61F 2/30*     (2006.01)

(52) U.S. Cl.
    CPC ............... *A61F 2002/4627* (2013.01); *A61F 2310/00023* (2013.01)

(56) References Cited

U.S. PATENT DOCUMENTS

| | | | |
|---|---|---|---|
| 2004/0059421 A1* | 3/2004 | Glenn | A61F 2/4611 623/17.16 |
| 2005/0113920 A1* | 5/2005 | Foley | A61F 2/4455 623/17.11 |
| 2006/0004455 A1* | 1/2006 | Leonard | A61F 2/44 623/17.15 |
| 2008/0140207 A1* | 6/2008 | Olmos | A61F 2/4455 623/17.16 |
| 2013/0325128 A1* | 12/2013 | Perloff | A61F 2/4455 623/17.16 |

* cited by examiner

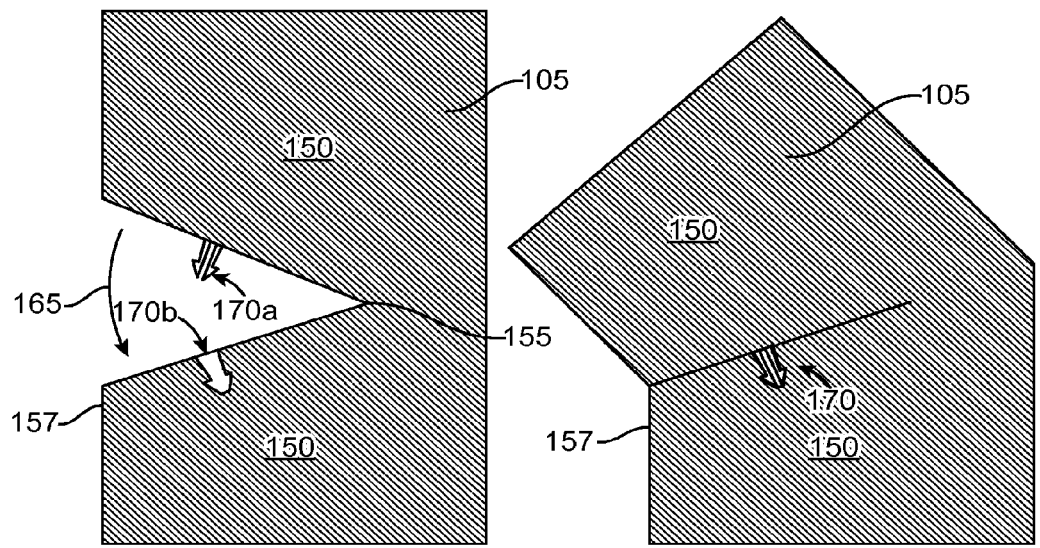
FIG. 5A
FIG. 5B
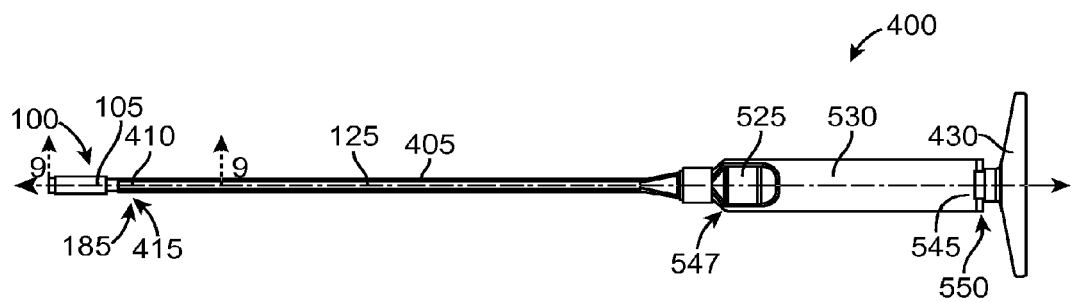
FIG. 6

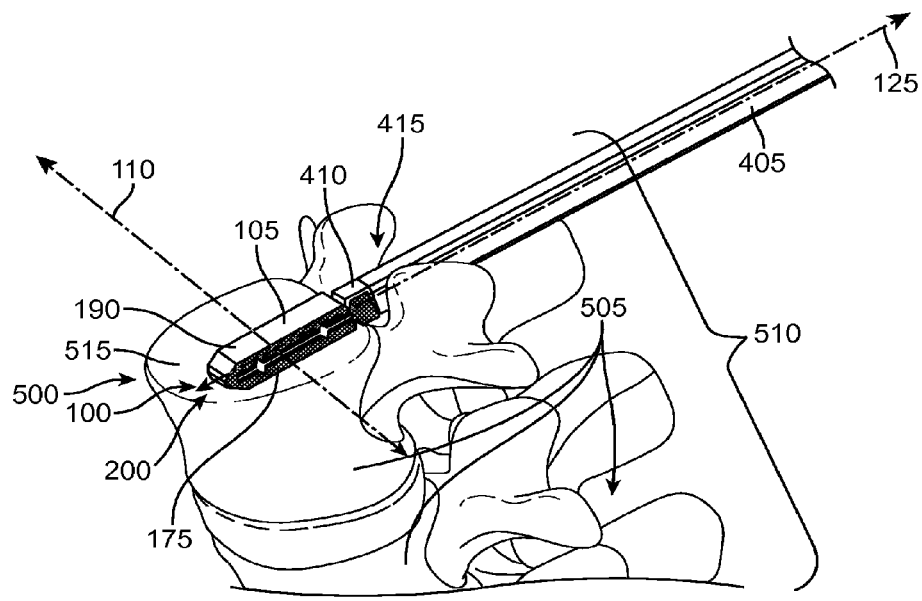
FIG. 11
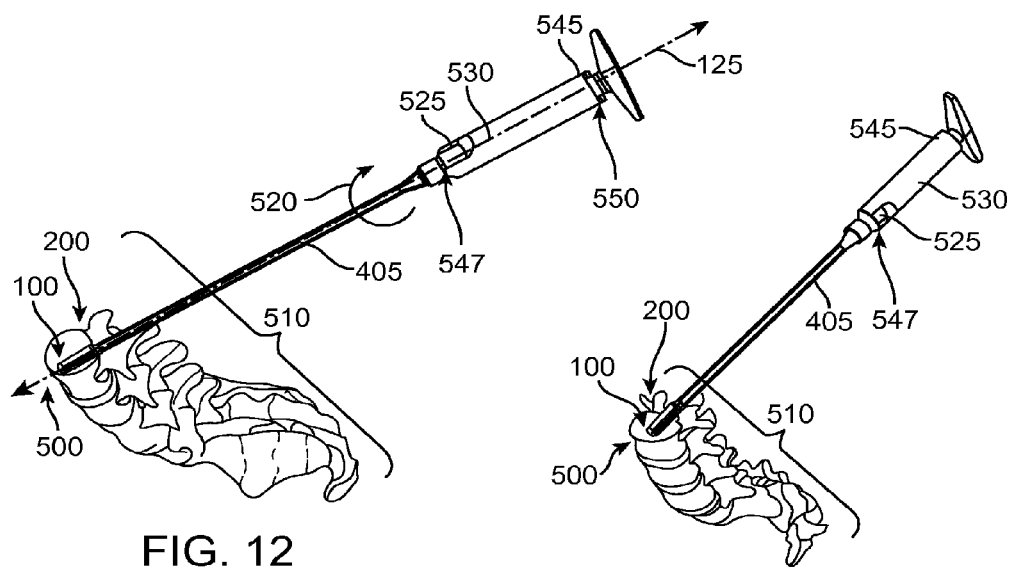
FIG. 12
FIG. 13

MINIMALLY INVASIVE INTERVERTEBRAL SYSTEMS AND METHODS

CROSS-REFERENCE TO RELATED APPLICATIONS

The present application is a divisional application of U.S. patent application Ser. No. 13/248,747, filed Sep. 29, 2011, which claims priority to U.S. Provisional Patent Application No. 61/389,986, filed Oct. 5, 2010, the entire contents of both of which are hereby expressly incorporated by reference.

FIELD

The present invention relates generally to a device for treating intervertebral injuries and, more specifically relates to a minimally invasive intervertebral implant that is plastically deformable to enhance bone graft volume and contact with vertebral endplates.

BACKGROUND

Current intervertebral devices are designed using three major principles: the anatomical limitations of the surgical approach, optimization of bone graft volume to promote bony fusion, and optimization of the device contact with vertebral endplates to resist subsidence. Current devices are generally static in that they cannot change shape or volume. Thus, current devices are limited by anatomy and technique and consequently may not provide optimal bone graft volume or surface contact.

A need exists for an intervertebral device or implant that can change shape and/or volume. Such a device benefits from the ability to be advanced to an implantation site in a first configuration having a reduced transverse dimension and subsequently transitioned to a second configuration having a desired transverse dimension at the implantation site. Such a device benefits from a rigid structure that can be held in the second configuration by plastic deformation of the material and/or a mechanism for locking the device in the second configuration. Such a device further benefits from being quickly implantable by a simple tool that places and positions the implant at the implantation site and further delivers bone graft material to fill an interior volume of the implant.

SUMMARY OF THE INVENTION

In one aspect of the present invention, a minimally invasive intervertebral implant includes a circuitous body defining a luminal axis extending longitudinally therethrough. The circuitous body includes proximal and distal ends oppositely disposed along a lateral axis of the circuitous body. Each of the proximal and distal ends includes an aperture disposed therethrough such that the circuitous body includes a first configuration wherein the proximal and distal ends are at a maximum separation and a second configuration wherein the proximal and distal ends are closer together than in the first configuration.

In another aspect of the present invention, a minimally invasive intervertebral implant system includes the minimally invasive intervertebral implant and an implantation tool includes a cannula including a pair of prongs extending distally from a distal end thereof. A shaft is adapted to be slidably disposed longitudinally through the cannula and includes a threaded distal end. A handle is attached to a proximal end of the shaft. The system may further include a funnel having a distal end adapted to removably attach to a proximal end of the cannula and a plunger adapted to form a sliding seal with a lumen of the funnel for the purpose of forcing bone graft material through the cannula.

In a further aspect of the present invention, a method for implantation of a minimally invasive intervertebral implant utilizing an implantation tool is presented. The method comprises the steps of attaching the minimally invasive vertebral implant in the first configuration to the threaded distal end of the shaft such that the pair of prongs engages the pair of proximally extending slots and advancing the distal end of the shaft toward an implantation site such that the luminal axis of the circuitous body is generally parallel with a bone surface at the implantation site. The method further includes the steps of rotating the cannula by about 90 degrees such that the luminal axis is generally perpendicular to the bone surface, translating the shaft proximally relative to the cannula to transition the minimally invasive vertebral implant from the first configuration to the second configuration, and detaching the implantation tool from the minimally invasive vertebral implant. The method may further include detaching the shaft from the minimally invasive vertebral implant by rotating the handle relative to the cannula, withdrawing the shaft from the cannula, connecting the funnel to the proximal end of the cannula, and forcing bone graft material through the funnel and cannula with the plunger until an interior volume of the minimally invasive vertebral implant is filled.

BRIEF DESCRIPTION OF THE FIGURES

FIG. 5A illustrates a living hinge having a locking mechanism in an open position.

FIG. 5B illustrates the living hinge of FIG. 5A in a locked position.

FIG. 6 illustrates a minimally invasive intervertebral implant attached to an embodiment of an implantation tool.

FIG. 11 illustrates an embodiment of a minimally invasive intervertebral implant positioned at an implantation site such that a luminal axis of the implant is generally parallel with a bone surface at the implantation site.

FIG. 12 illustrates the minimally invasive intervertebral implant at the implantation site of FIG. 11 before rotation.

FIG. 13 illustrates the minimally invasive intervertebral implant at the implantation site of FIG. 11 after rotation such that the luminal axis of the implant is generally perpendicular to the bone surface.

The foregoing and other features and advantages of the invention are apparent from the following detailed description of exemplary embodiments, read in conjunction with the accompanying drawings; wherein like structural or functional elements may be designated by like reference numerals.

DETAILED DESCRIPTION

The words proximal and distal are applied to denote specific ends of components of the current invention described herein. A proximal end refers to the end of a component nearer to a medical professional when the component is implanted. A distal end refers to the end of a component further from the medical professional when the component is implanted.

Figure 1:
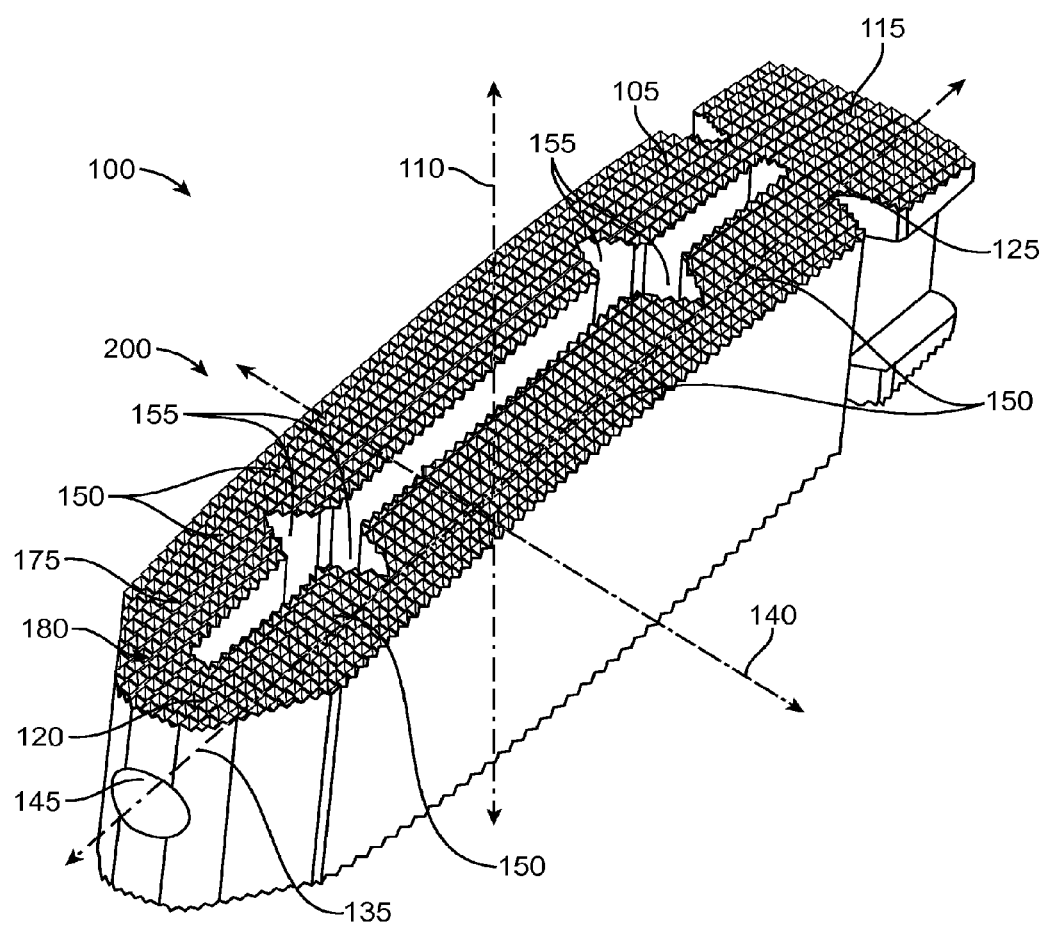
FIG. 1 is an isometric view of an embodiment of a minimally invasive intervertebral implant in a first configuration.

Referring to FIGS. 1-4, an embodiment of a minimally invasive intervertebral implant 100 includes a circuitous body 105 defining a luminal axis 110 extending longitudinally therethrough, as illustrated in FIG. 1. The circuitous body 105 includes a proximal end 115 and a distal end 120 that are oppositely disposed along a lateral axis 125 of the circuitous body 105. As best visible in FIG. 2C, a proximal aperture 130 is disposed through the proximal end 115 of the circuitous body 105 and a distal aperture 135 is disposed through the distal end 120 of the circuitous body 105. A transverse axis 140 that is orthogonal to the luminal axis 110 and the lateral axis 125, as illustrated in FIG. 1, is defined for convenience of description herein. In one embodiment, threads (not shown) are disposed on a luminal surface 145 of the distal aperture 135.

Figure 2A:
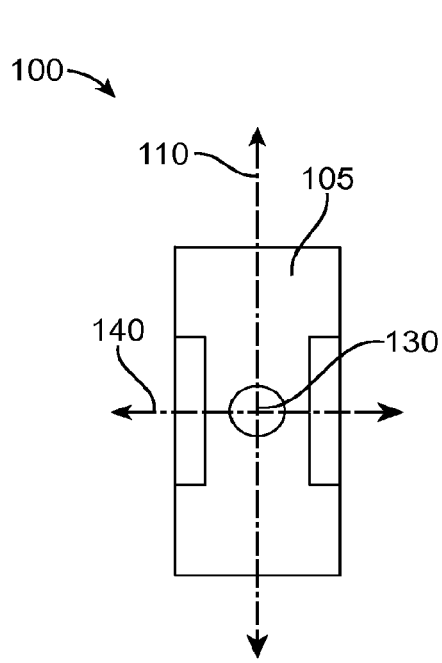
FIG. 2A is a lateral elevation of the minimally invasive intervertebral implant of FIG. 1 in the first configuration.
Figure 2B:
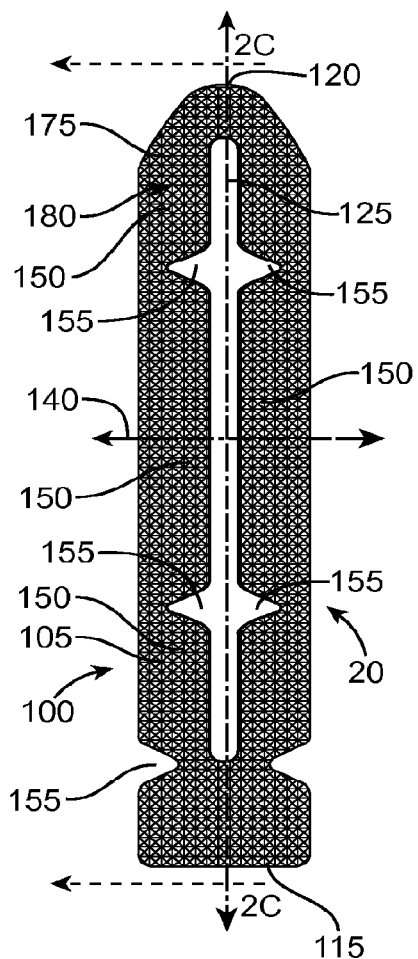
FIG. 2B is a luminal elevation of the minimally invasive intervertebral implant of FIG. 1 in the first configuration.
Figure 2C:
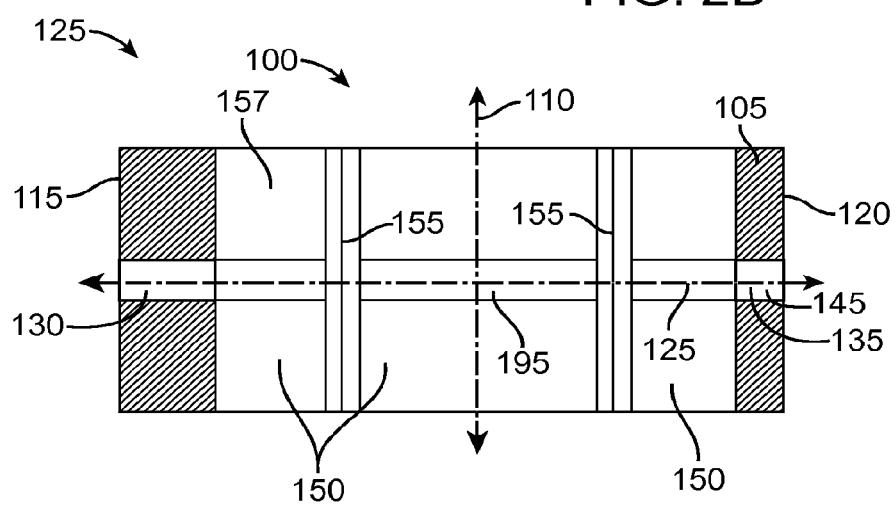
FIG. 2C is a cross-sectional view of the minimally invasive intervertebral implant, taken generally along the line 2C-2C of FIG. 2B.
Figure 3:
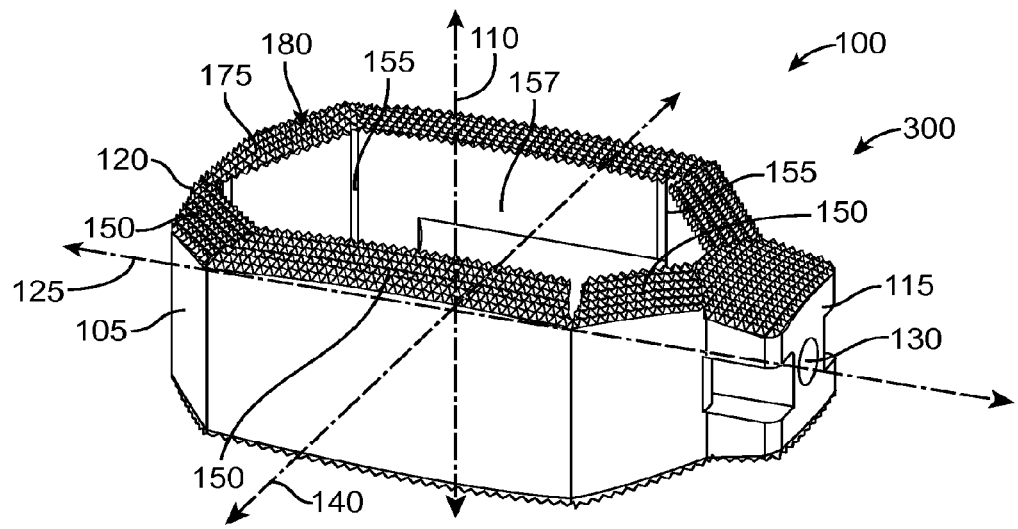
FIG. 3 is an isometric view of the minimally invasive intervertebral implant of FIG. 1 in a second configuration.
Figure 4:
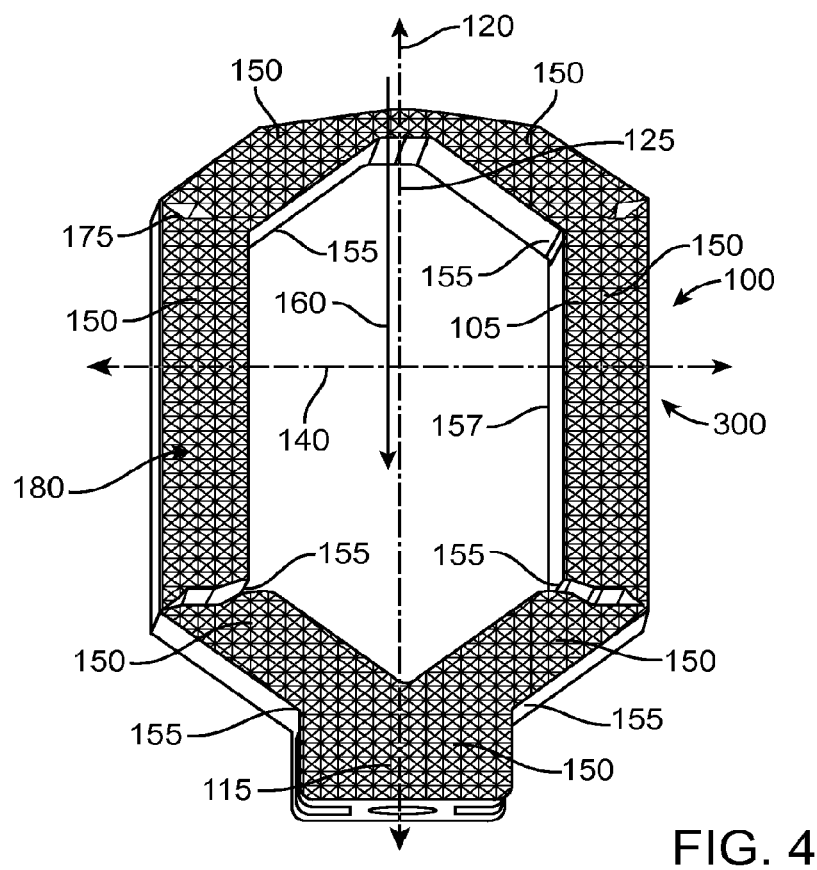
FIG. 4 is a luminal elevation of the minimally invasive intervertebral implant of FIG. 1 in the second configuration.
Figure 7:
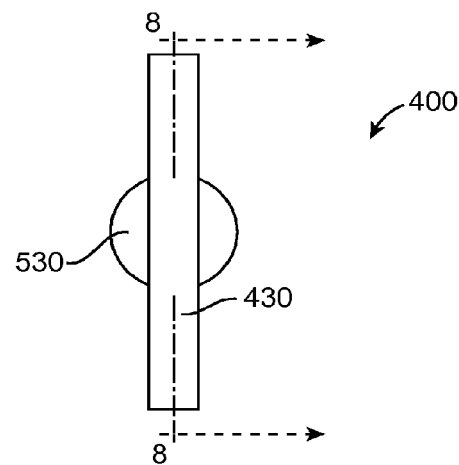
FIG. 7 is a proximal elevation of the implantation tool of FIG. 6.
Figure 8:
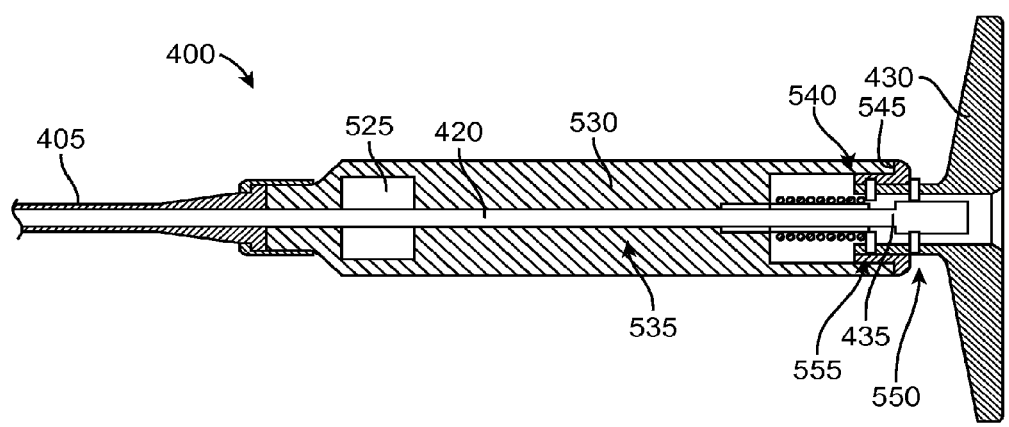
FIG. 8 is a cross-sectional view of the implantation tool, taken generally along the line 8-8 of FIG. 7.
Figure 9:
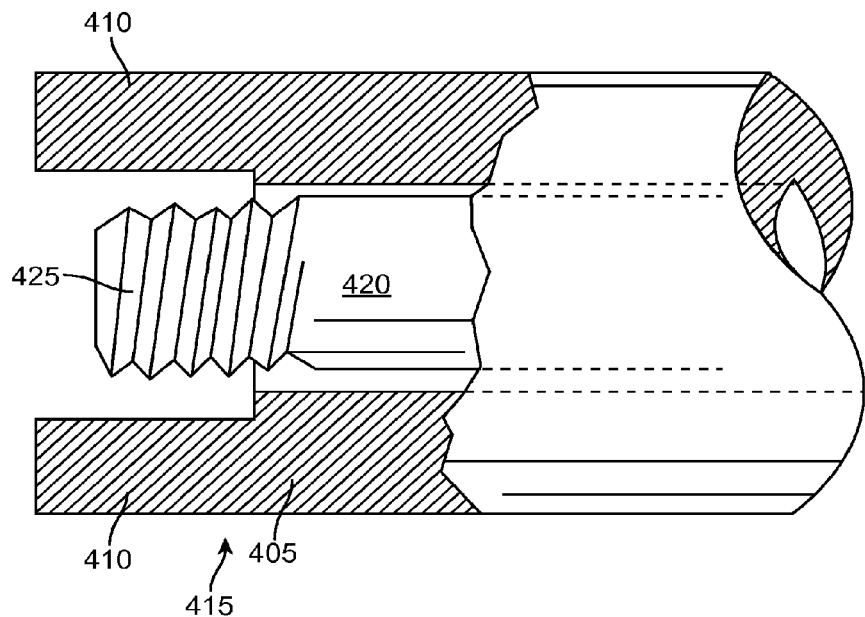
FIG. 9 is an enlarged cross-sectional view of a distal end of the implantation tool, taken generally along the line 9-9 of FIG. 6.

The circuitous body 105 includes a first configuration 200 wherein the proximal and distal ends 115, 120 are at a maximum separation, as best illustrated by FIGS. 1 and 2B. Referring to FIGS. 3 and 4, the circuitous body 105 includes a second configuration 300 wherein the proximal and distal ends 115, 120 are separated by less than a maximum separation and are therefore closer together than in the first configuration. The circuitous body 105 may be held in the second configuration by plastic deformation of the material.

In one embodiment, the circuitous body 105 comprises a rigid biologically inert material, including by way of example and not limitation, titanium, titanium alloy, and polyetherketoneketone (PEEK). The circuitous body 105 may transition from the first configuration 200 to the second configuration 300 via elastic or plastic deformation. It is preferable that the circuitous body 105 maintains the second configuration 300 subsequent to a transition thereto as would be the case if the transition from the first configuration 200 to the second configuration 300 plastically deforms the circuitous body 105. Applying sufficient force on the distal end 120 toward the proximal end 115, as depicted by arrow 160 in FIG. 4, causes the circuitous body 105 to transition from the first configuration 200 to the second configuration 300.

Referring to FIGS. 1, 2B, 3, and 4, in one embodiment, the circuitous body 105 comprises a single piece unit having segments 150 that are linked by living hinges 155 that are disposed in an interior surface 157 of the circuitous body 105 and that may plastically deform in the transition from the first configuration 200 to the second configuration 300. As illustrated in FIGS. 1, 2B, and 5A, when the circuitous body 105 is in the first configuration 200, the living hinges 155 are in an open position. As illustrated in FIGS. 3, 4, and 5B, upon transition to the second configuration 300, the segments 150 rotate relative to one another, as depicted by the arrow 165 in FIG. 5A, such that the living hinges 155 are in a closed position.

In some embodiments, plastic deformation of the living hinges 155 from the open position as illustrated in FIGS. 1, 2B, and 5A to the closed position as illustrated in FIGS. 3, 4, and 5B may provide sufficient plastic deformation such that the circuitous body 105 maintains the second configuration 300 subsequent to a transition thereto. In other embodiments, a locking mechanism 170, for example, male and female compressive snap fittings 170a, 170b, may be provided, as illustrated in FIGS. 5A and 5B. In this embodiment, barbed ends of the male compressive snap fitting 170a are compressed toward one another upon entry into the female compressive snap fitting 170b. Ultimately, as the segments 150 rotate such that the living hinge 155 reaches the closed position as illustrated in FIGS. 3, 4, and 5B, the barbed ends of the male compressive snap fitting reach a depth beyond a set of internal shoulders within the female compressive snap fitting at which point the barbed ends spring apart and are permanently captured by the internal shoulders.

Other locking mechanisms 170 may be utilized to maintain the circuitous body 105 in the second configuration 300 subsequent to a transition thereto, including by way of example and not limitation, contact adhesive, a single barbed male fitting engaging a female fitting, etc. It is contemplated that the locking mechanism 170 may also comprise a ratchet mechanism (not shown), whereby the female compressive snap fitting 170b includes multiple sets of internal shoulders at increasing depths such that the living hinge 155 can be locked in any of several positions between a fully open position as illustrated in FIGS. 1, 2B, and 5A and a fully closed position as illustrated in FIGS. 3, 4, and 5B.

Referring to FIGS. 1, 2B, 3, and 4, in some embodiments, at least one longitudinally facing surface 175 of the circuitous body 105 includes a texture 180 adapted to enhance fixed contact with a bone surface. Further, referring to FIGS. 1, 2A and 3, the proximal end 115 of the circuitous body 105 includes a pair of proximally extending slots 185 oppositely disposed in exterior surfaces 190 of the proximal end 115. As will be fully described hereinbelow, the slots 185 are adapted to accommodate prongs (See FIGS. 6 and 9-11) of an implantation tool (See FIGS. 6-9, 12, 13, and 16).

Figure 16:
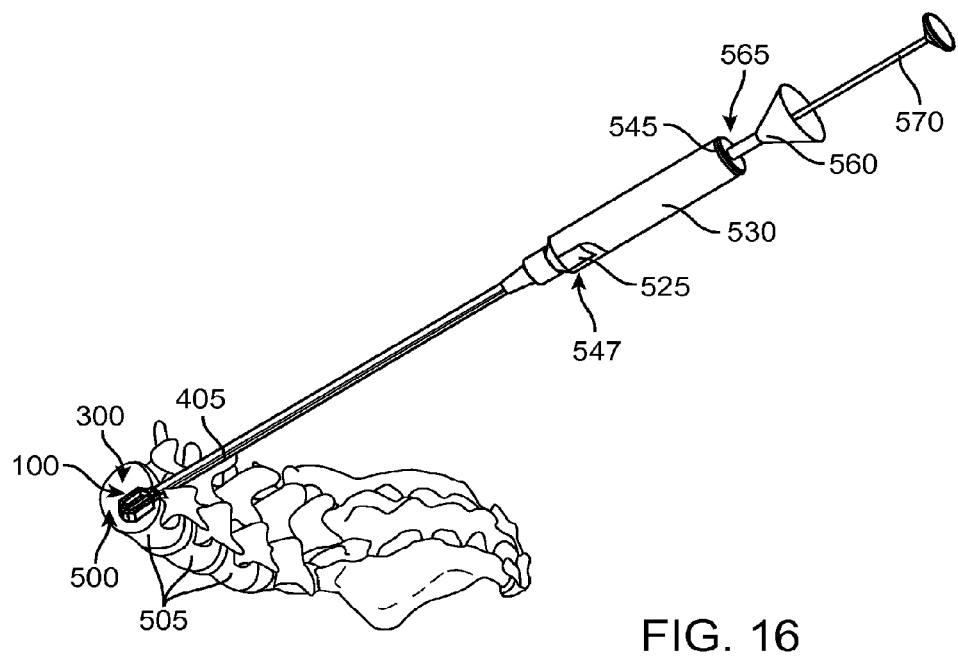
FIG. 16 illustrates the minimally invasive intervertebral implant at the implantation site of FIG. 11 in the second configuration being filled with bone graft material by the implantation tool with the shaft and handle replaced by a funnel and plunger.

Referring to FIGS. 6-9, an embodiment of an implantation tool 400 for the minimally invasive intervertebral implant 100 includes a cannula 405 having a pair of prongs 410 extending distally from a distal end 415 of the cannula 405 to engage the slots 185 in the circuitous body 105. Referring to FIGS. 8-10D, the implantation tool 400 includes a shaft 420 adapted to be slidably disposed longitudinally through the cannula 405. In one embodiment, the shaft 420 includes a threaded distal end 425 adapted to engage threads (not shown) disposed on the luminal surface 145 of the distal aperture 135 of the circuitous body 105. In other embodiments, the distal end 425 includes other removable fastening mechanisms for attachment to the luminal surface 145 of the distal aperture 135, including by way of example and not limitation, a keyed aperture, a bayonet slot, and the like. A handle 430 is attached to a proximal end 435 of the shaft 420. Referring to FIG. 16, the implantation tool 400 further includes a plunger and a funnel, which will be fully described hereinbelow with regard to a method for implantation of the minimally invasive intervertebral implant 100.

Figure 10A:
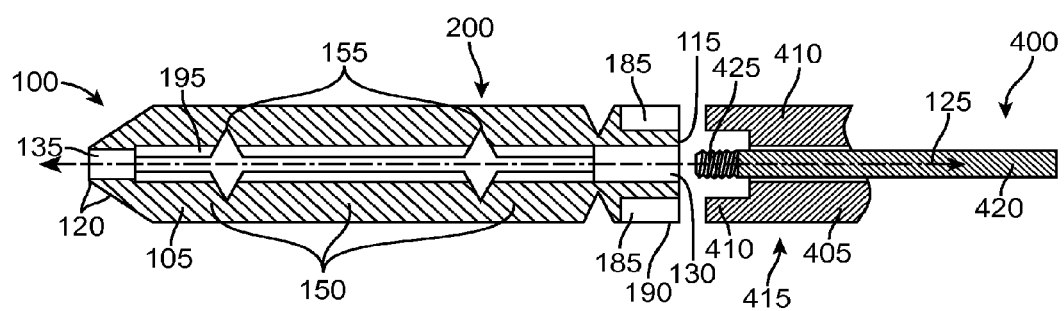
FIG. 10A is a cross-sectional view of the minimally invasive intervertebral implant in the first configuration and the distal end of the implantation tool prior to attachment, taken generally along the line 9-9 of FIG. 6.

As illustrated in FIGS. 10A-10D, the implantation tool 400 functions to transition the circuitous body 105 from the first configuration 200 to the second configuration 300. Further, as illustrated in FIGS. 11-16, the implantation tool 400 functions to facilitate placement, orientation, and filling of the minimally invasive intervertebral implant 100 at an implantation site. Referring to FIG. 10A, in a first step, the minimally invasive vertebral implant 100 is in the first configuration 200. The distal end 415 of the cannula 400 is brought near the proximal end 115 of the circuitous body 105 such that the pair of prongs 410 is aligned with the pair of slots 185. Next, the cannula 405 is advanced distally relative to the minimally invasive intervertebral implant 110, as illustrated by arrow 440 in FIG. 10B, such that the pair of prongs 410 engages the pair of proximally extending slots 185.

Figure 10B:
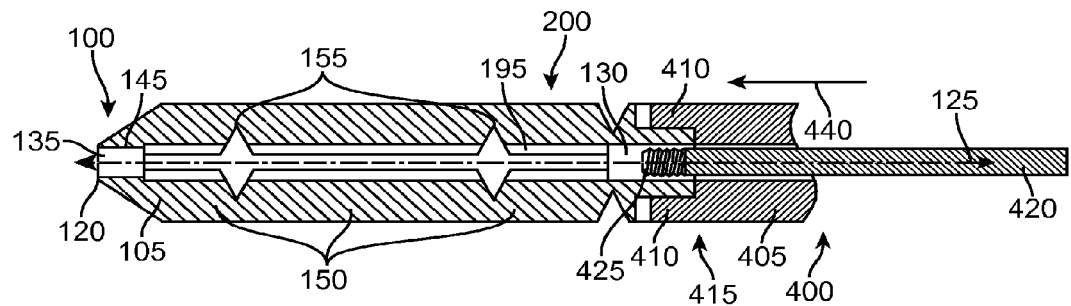
FIG. 10B is the view of FIG. 10A illustrating the prongs of the implantation tool engaging the slots of the minimally invasive intervertebral implant.

At the point in the method illustrated in FIG. 10B, the cannula 405 is connected to the proximal end 115 of the circuitous body 105 such that rotation of the cannula 405 results in rotation of the circuitous body 105. Such rotation is independent of the shaft 420 that is free to rotate and translate along the lateral axis 135 within the cannula 405.

Figure 10C:
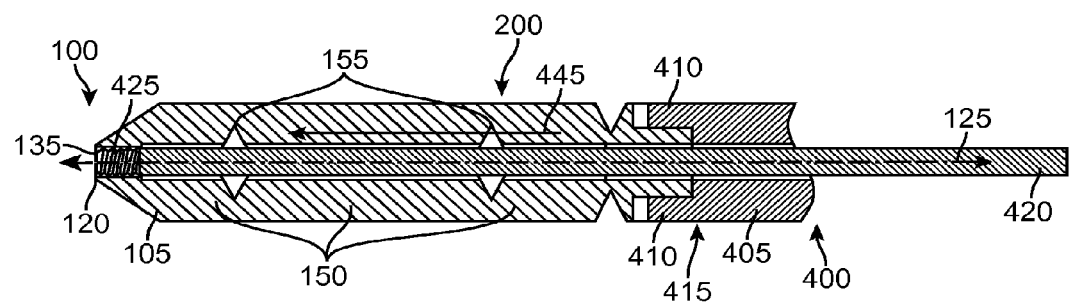
FIG. 10C is the view of FIG. 10B illustrating the threaded tip of the shaft of the implantation tool engaging the distal aperture of the minimally invasive intervertebral implant.

Referring to FIG. 10C, the shaft 420 is advanced distally relative to the cannula 405 such that the distal end 425 of the shaft 420 passes through the proximal aperture 130. Referring to FIGS. 2C, 10A, 10B, and 10D, in one embodiment, an internal groove 195 is disposed extending laterally along the lateral axis 125 in the interior surface 157 of the circuitous body 105. The internal groove 195 provides clearance for the shaft 420 passing across the circuitous body from the proximal aperture 130 to the distal aperture 135. Such clearance allows the circuitous body 105 to be transversely compressed in the first configuration 200. Such transverse compression may allow the circuitous body 105 to fit into a smaller space, for example, an intervertebral space, than might be possible if the internal groove 195 were not present.

Figure 10D:
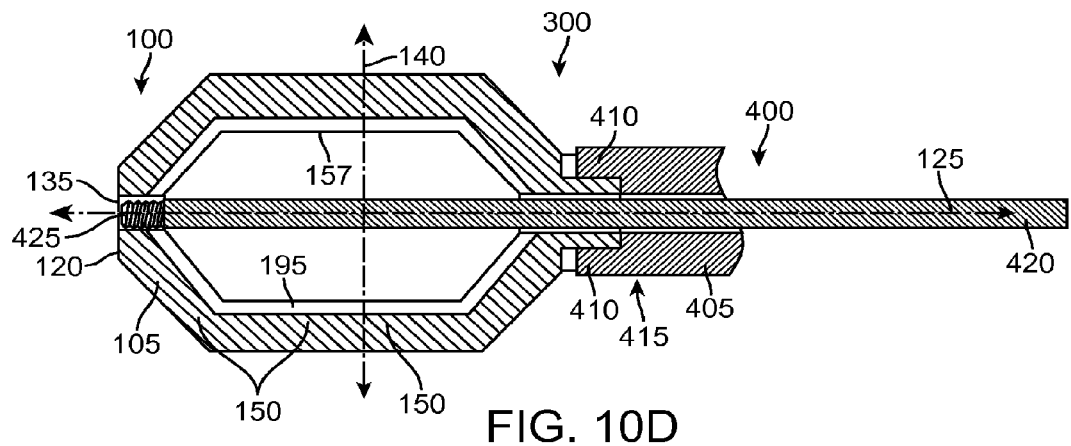
FIG. 10D is the view of FIG. 10C illustrating the minimally invasive intervertebral implant transitioned to the second configuration.

The shaft 420 is further advanced distally relative to the cannula 405, as illustrated by arrow 445 in FIG. 10C, until the distal end 425 passes into the distal aperture 135. In this embodiment, the distal end 425 and the luminal surface 145 of the distal aperture 135 may threadably engage via rotation of the shaft 420 relative to the cannula 405 using the handle 430 that is attached to the proximal end 435 of the shaft 420. Referring to FIG. 10D, following connection of the distal end 425 of the shaft 420 to the distal aperture 135, a force is applied to the shaft 420 in a proximal direction relative to the cannula 405. In this embodiment, the force is transmitted as a tension force within the shaft 420 effectively applying a laterally compressive force to the circuitous body 105 between the distal aperture 135 and the proximal end 115. Subsequent to transitioning the circuitous body 105 from the first configuration 200 to the second configuration 300, the distal end 425 of the shaft 420 is disconnected from the distal aperture 135 and removed from the cannula 405.

Having described how the implantation tool 400 functions to transition the circuitous body 105 from the first configuration 200 to the second configuration 300 hereinabove with regard to FIGS. 10A-10D, the function of the implantation tool 400 for placement, orientation, and filling of the minimally invasive intervertebral implant 100 at an implantation site will now be described. Referring to FIG. 11, in a first step, the distal end 415 of the implantation tool 400, including the minimally invasive intervertebral implant 100 attached thereto in the first configuration 200 with the distal end 425 of the shaft 420 engaging the distal aperture 135, is advanced to an implantation site 500, for example, at a space between vertebrae 505 of a spine 510. The minimally invasive intervertebral implant 100 is oriented at the implantation site 500 such that the luminal axis 110 of the circuitous body 105 is generally parallel with a bone surface 515 at the implantation site 500.

One reason why the circuitous body 105 is initially oriented as illustrated in FIG. 11 is the relative ease of introduction into an intervertebral space facilitated by such orientation. As known in the art, prior to placement of the minimally invasive intervertebral implant 100 in the intervertebral space, vertebrae on either side of the intervertebral space are distracted. In some methodologies, distraction is accomplished via a tool having paddles that can get in between the vertebrae and can subsequently be spread apart to distract the vertebrae. A tool that may be useful in distracting the vertebrae may, for example, be found in Reindel et al. U.S. Patent Application Publication No. 2009/0306672, which is incorporated by reference herein in its entirety.

Following distraction of the vertebrae, a common procedure includes preparing the intervertebral disc space for introduction of an implant. Preparation may include removal of a portion of a disc annulus or evacuation of a disc nucleus, as known in the art. Further steps may include the removal of cartilaginous endplates on the vertebrae. A tool that may be useful in preparation of an intervertebral disc space for introduction of an implant may be found, for example, in Jansen et al. U.S. Pat. No. 7,632,278, which is incorporated by reference herein in its entirety.

As noted hereinabove, with regard to FIGS. 2C, 10A, 10B, and 10D and the internal groove 195, transverse compression of the circuitous body 105 may allow the circuitous body 105 to fit into a smaller intervertebral space than might be possible if the internal groove 195 were not present. The ability to fit the circuitous body in a smaller space facilitates less distraction of the surrounding vertebrae. Thus, the circuitous body 105 is introduced into the intervertebral disc space such that the exterior surfaces 190 initially face the bone surface 515 and the longitudinally facing surfaces 175 do not face the bone surface 515.

Figures 14, 15:
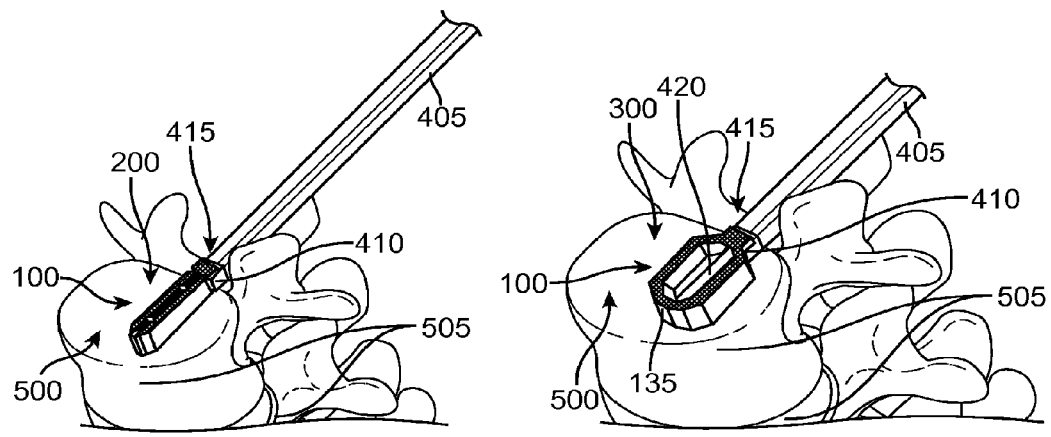
FIG. 14 illustrates the minimally invasive intervertebral implant at the implantation site of FIG. 11 after rotation and prior to being transitioned from the first configuration to the second configuration.
FIG. 15 illustrates the minimally invasive intervertebral implant at the implantation site of FIG. 11 in the second configuration prior to being filled with bone graft material.

Referring to FIGS. 12 and 13, subsequent to initial placement of the minimally invasive intervertebral implant 100, the circuitous body 105 is rotated by about 90 degrees, as illustrated by arrow 520 in FIG. 12. FIGS. 13 and 14 illustrate the circuitous body 105 subsequent to rotation and in an orientation such that the longitudinally facing surfaces 175 face the bone surface 515 and the exterior surfaces 190 do not face the bone surface 515.

Referring to FIGS. 6, 8, 12, 13, and 16, in some embodiments, the implantation tool may include a rotational position indicator 525 that is fixedly attached to the cannula 405. Because the cannula is rotationally fixed to the circuitous body 105 via the prongs 410 engaged in the slots 185, the relative rotational position of the circuitous body 105 is reflected by the relative rotational position of the rotational position indicator 525.

Still referring to FIGS. 6, 8, 12, 13, and 16, in another embodiment, the implantation tool 400 may further include a cover member 530 that attaches over a proximal end 535 of the cannula 405 such that a distal end 540 of the handle 430 is accommodated by a proximal end 545 of the cover member 530. The cover member 530 provides a larger surface that may be easier to grab and manipulate by a medical professional. In addition, the cover member is rotationally fixed to the cannula 405 and may include an aperture 547 through which the rotational position indicator is visible.

First and second positional markings 550, 555 are disposed proximate the distal end 540 of the handle 430. When the first marking 550 is visible and the second marking 555 is visibly obstructed by the cover member 530, the distal end 425 of the shaft 420 extends from the distal end 415 of the cannula 405 a first distance that may, for example, correspond to the shaft 420 being operationally attached to the distal aperture 135 of the circuitous body 105 in the first configuration 200. When the first and second markings 550, 555 are both visible, the distal end 425 of the shaft 420 extends from the distal end 415 of the cannula 405 a second distance that may, for example, correspond to the shaft 420 being operationally attached to the distal aperture 135 of the circuitous body 105 in the second configuration 300. Thus, the first and second markings 550, 555 may provide a medical practitioner a visual aide in addition to visualization of the implantation site 500 via other methods known in the art to determine the status of the circuitous body 105.

Referring again to FIG. 14, the circuitous body 105 is oriented appropriately to undergo transition from the first configuration 200 to the second configuration 300. As illustrated in FIG. 15 and described in detail hereinabove with regard to FIGS. 10A-10D, the circuitous body 105 is transitioned from the first configuration 200 to the second configuration 300 by applying a lateral compression force between the proximal and distal ends thereof.

Referring to FIG. 16, following delivery and orientation of the circuitous body 105 and transition to the second configuration 300, the shaft 420 and handle 430 are removed from the cannula 405, as described in detail hereinabove in regard to FIGS. 10A-10D. In one embodiment, the implantation tool 400 includes a funnel 560 having a distal end 565 adapted to removably attach to the proximal end 535 of the cannula 405. The funnel 560 may attach to the cannula 405 by any method of attachment as known in the art, including by way of example and not limitation, a press fit, a snap fit, a bayonet socket, threads, and the like.

A plunger 570 is adapted to form a sliding seal with a lumen of the funnel 560 for the purpose of forcing bone graft material through the cannula 405 to the implantation site 500 within the circuitous body 105. Thus, in a final step in the method for implantation of a minimally invasive intervertebral implant, bone graft material is forced through the funnel 560 and cannula 405 with the plunger 570 until an interior volume of the minimally invasive vertebral implant 100 is filled.

A minimally invasive intervertebral implant, an implantation tool therefore, and a method for implantation thereof are presented. The implant benefits from the having an expandable geometry, which allows the implant to be placed into intervertebral spaces smaller than typical fixed geometry implants.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the minimally invasive intervertebral implant, implantation tool therefor, and method for implantation thereof described herein and to teach the best mode of carrying out the same.

The invention claimed is:

1. A method for implantation of a minimally invasive intervertebral implant using an implantation tool, comprising:

attaching the minimally invasive vertebral implant in a first configuration to a threaded distal end of a shaft of the implantation tool and engaging a pair of prongs on a cannula of the implantation tool to a pair of proximally extending slots on the implant, the implant comprising:
a circuitous body defining a luminal axis extending longitudinally therethrough;
proximal and distal ends oppositely disposed along a lateral axis of the circuitous body; and
advancing the distal end of the shaft toward an implantation site such that the luminal axis of the circuitous body of the implant is generally parallel with a bone surface at an implantation site;
rotating the cannula by about 90 degrees such that the luminal axis is generally perpendicular to the bone surface;
translating the shaft proximally relative to the cannula to transition the minimally invasive vertebral implant from the first configuration to a second configuration, wherein in the first configuration the proximal and distal ends are at a maximum separation and in the second configuration the proximal and distal ends are closer together than in the first configuration; and
detaching the implantation tool from the minimally invasive vertebral implant.

2. The method for implantation of claim 1, wherein the circuitous body comprises segments linked by living hinges that plastically deform in the transition from the first configuration to the second configuration.

3. The method for implantation of claim 1, further comprising:
connecting a funnel to a proximal end of the cannula; and forcing bone graft material through the funnel into an interior volume of the minimally invasive vertebral implant in the second configuration.

4. The method for implantation of claim 1, wherein the implantation site is an intervertebral disc space and includes the following steps prior to the attaching step:
accessing the intervertebral disc space;
distracting adjacent vertebrae on either side of the intervertebral disc space; and
preparing the intervertebral disc space.

5. The method for implantation of claim 2, wherein at least one of the living hinges include a locking mechanism on adjacent hinged segments for locking the device in the closed position comprising male and female compressive snap fittings.

6. The method for implantation of claim 1, wherein the circuitous body comprises a rigid biologically inert material selected from the group consisting of: titanium, titanium alloy, and polyetheretherketone.

7. A method for implantation of a minimally invasive intervertebral implant using an implantation tool, comprising:
attaching the minimally invasive vertebral implant to the implantation tool, the implant comprising:
a circuitous body defining a luminal axis extending longitudinally therethrough, the circuitous body comprising a plurality of segments having longitudinally facing surfaces and exterior surfaces;
proximal and distal ends oppositely disposed along a lateral axis of the circuitous body, the proximal end having an aperture for receiving the implantation tool; and
wherein the circuitous body includes:
a first configuration wherein the proximal and distal ends are at a maximum separation; and
a second configuration wherein the proximal and distal ends are closer together than in the first configuration and wherein the distal end forms the distalmost end of the implant;
engaging prongs on a cannula of the implantation tool to the proximal end on the implant;
inserting the implant between adjacent vertebrae at an implantation site such that the luminal axis of a circuitous body of the implant is generally parallel with a bone surface at an implantation site;
rotating the cannula by about 90 degrees such that the luminal axis is generally perpendicular to the bone surface;
transitioning the implant from the first configuration to the second configuration between adjacent vertebrae;
detaching the implantation tool from the minimally invasive vertebral implant.

8. The method for implantation of claim 7, wherein the plurality of segments are linked by living hinges configured to deform in transition from an open position to a closed position, at least one of the living hinges include a locking mechanism on adjacent hinged segments for locking the device in the closed position comprising male and female compressive snap fittings.

9. The method for implantation of claim 7, wherein the proximal end includes a pair of proximally extending slots adapted to accommodate prongs of the implantation tool.

10. The method for implantation of claim 7, wherein the circuitous body comprises a rigid biologically inert material selected from the group consisting of: titanium, titanium alloy, and polyetheretherketone.

11. The method for implantation of claim 7, further comprising:
connecting a funnel to a proximal end of the cannula; and
forcing bone graft material through the funnel into an interior volume of the minimally invasive vertebral implant in the second configuration.

12. The method for implantation of claim 7, wherein the in/plantation site is an intervertebral disc space and includes the following steps prior to the attaching step:
accessing the intervertebral disc space;
distracting adjacent vertebrae on either side of the intervertebral disc space; and
preparing the intervertebral disc space.

13. The method for implantation of claim 7, further including a rotational position indicator fixedly attached to the cannula.

14. The method for implantation of claim 7, wherein an external cover attaches over a proximal end of the cannula, wherein first and second positional markings are disposed proximate the distal end of the handle such that when the first marking is visible and the second marking is visibly obstructed by the cover, the distal end of the shaft extends from the cannula a first distance, and when the first and second markings are visible the distal end of the shaft extends from the cannula a second distance.

15. A method for implantation of a minimally invasive intervertebral implant using an implantation tool, comprising:
attaching the minimally invasive vertebral implant to the implantation tool, the implant comprising:
a circuitous body defining a luminal axis extending longitudinally therethrough, the circuitous body comprising a plurality of segments linked by living hinges configured to deform in transition from an open position to a closed position, at least one of the living hinges include a locking mechanism on adjacent hinged segments for locking the device in the closed position comprising male and female compressive snap fittings, the segment having exterior surfaces and longitudinally facing surfaces;
wherein the circuitous body includes:
a first configuration wherein the proximal and distal ends are at a maximum separation; and
a second configuration wherein the proximal and distal ends are closer together than in the first configuration and wherein the distal end forms the distal most end of the implant;
inserting the implant between adjacent vertebrae with the implantation tool at an implantation site such that the luminal axis of a circuitous body of the implant is generally parallel with a bone surface at an implantation site;
rotating the implantation tool by about 90 degrees within the implantation site;
transitioning the implant from the first configuration to the second configuration between adjacent vertebrae.

16. The method for implantation of claim 15, wherein the proximal end includes an aperture for receiving the implantation tool, the implantation tool comprising:
a cannula including a pair of prongs extending distally from a distal end thereof, the pair of prongs configured to engage slots on the proximal end of the implant;
a shaft adapted to be slidably disposed longitudinally through the cannula having a threaded distal end configured to engage the distal end of the implant, wherein the distal end of the shaft extends from the distal end of the cannula; and a handle attached to a proximal end of the shaft;
the method further comprising:
  engaging prongs of the implantation tool to the aperture on the implant;
  applying a force on the circuitous body from the distal end of the implant to the proximal end to transition the circuitous body from the first configuration to the second configuration; and
  detaching the implantation tool from the minimally invasive vertebral implant.

17. The method for implantation of claim 15, further comprising:
  connecting a funnel to a proximal end of the cannula; and
  forcing bone graft material through the funnel into an interior volume of the minimally invasive vertebral implant in the second configuration.

18. The method for implantation of claim 15, wherein the implantation site is an intervertebral disc space and includes the following steps prior to the attaching step:
  accessing the intervertebral disc space;
  distracting adjacent vertebrae on either side of the intervertebral disc space; and
  preparing the intervertebral disc space.

19. The method for implantation of claim 15, wherein the circuitous body comprises a rigid biologically inert material selected from the group consisting of: titanium, titanium alloy, and polyetheretherketone.

20. A method for implantation of a minimally invasive intervertebral implant using an implantation tool, comprising:
  attaching the minimally invasive vertebral implant in a first configuration to a distal end of a shaft of the implantation tool and engaging a pair of prongs on a cannula of the implantation tool to a pair of proximally extending slots on the implant;
  advancing the distal end of the shaft toward an implantation site such that a luminal axis of a circuitous body of the implant is generally parallel with a bone surface at an implantation site;
  rotating the cannula by about 90 degrees such that the luminal axis is generally perpendicular to the bone surface;
  translating the shaft proximally relative to the cannula to transition the minimally invasive vertebral implant from the first configuration to a second configuration;
  detaching the implantation tool from the minimally invasive vertebral implant
  connecting a funnel to a proximal end of the cannula; and
  forcing bone graft material through the funnel into an interior volume of the minimally invasive vertebral implant in the second configuration.

21. The method for implantation of claim 20, wherein the implant comprises:
  a circuitous body defining a luminal axis extending longitudinally therethrough;
  proximal and distal ends oppositely disposed along a lateral axis of the circuitous body; and
  wherein in the first configuration the proximal and distal ends are at a maximum separation and in the second configuration the proximal and distal ends are closer together than in the first configuration.

22. The method for implantation of claim 21, wherein the circuitous body comprises segments linked by living hinges that plastically deform in the transition from the first configuration to the second configuration.

23. The method for implantation of claim 20, wherein the implantation site is an intervertebral disc space and includes the following steps prior to the attaching step:
  accessing the intervertebral disc space;
  distracting adjacent vertebrae on either side of the intervertebral disc space; and
  preparing the intervertebral disc space.

24. The method for implantation of claim 23, wherein at least one of the living hinges include a locking mechanism on adjacent hinged segments for locking the device in the closed position comprising male and female compressive snap fittings.

25. The method for implantation of claim 20, wherein the circuitous body comprises a rigid biologically inert material selected from the group consisting of: titanium, titanium alloy, and polyetheretherketone.

26. A method for implantation of a minimally invasive intervertebral implant using an implantation tool, comprising:
  attaching the minimally invasive vertebral implant in a first configuration to a threaded distal end of a shaft of the implantation tool and engaging a pair of prongs on a cannula of the implantation tool to a pair of proximally extending slots on the implant, the implant comprising:
    a circuitous body defining a luminal axis extending longitudinally therethrough;
    wherein the circuitous body comprises segments linked by living hinges that plastically deform in the transition from the first configuration to the second configuration;
    proximal and distal ends oppositely disposed along a lateral axis of the circuitous body; and
  advancing the distal end of the shaft toward an implantation site such that the luminal axis of the circuitous body of the implant is generally parallel with a bone surface at an implantation site;
  rotating the cannula by about 90 degrees such that the luminal axis is generally perpendicular to the bone surface;
  translating the shaft proximally relative to the cannula to transition the minimally invasive vertebral implant from the first configuration to a second configuration, wherein in the first configuration the proximal and distal ends are at a maximum separation and in the second configuration the proximal and distal ends are closer together than in the first configuration; and
  detaching the implantation tool from the minimally invasive vertebral implant.

27. The method for implantation of claim 26, further comprising:
  connecting a funnel to a proximal end of the cannula; and
  forcing bone graft material through the funnel into an interior volume of the minimally invasive vertebral implant in the second configuration.

28. The method for implantation of claim 26, wherein the implantation site is an intervertebral disc space and includes the following steps prior to the attaching step:
  accessing the intervertebral disc space;
  distracting adjacent vertebrae on either side of the intervertebral disc space; and
  preparing the intervertebral disc space.

29. The method for implantation of claim 26, wherein at least one of the living hinges include a locking mechanism on adjacent hinged segments for locking the device in the closed position comprising male and female compressive snap fittings.

30. The method for implantation of claim 26, wherein the circuitous body comprises a rigid biologically inert material selected from the group consisting of: titanium, titanium alloy, and polyetheretherketone.

31. A method for implantation of a minimally invasive intervertebral implant using an implantation tool, comprising:

attaching the minimally invasive vertebral implant in a first configuration to a threaded distal end of a shaft of the implantation tool and engaging a pair of prongs on a cannula of the implantation tool to a pair of proximally extending slots on the implant, the implant comprising:
- a circuitous body defining a luminal axis extending longitudinally therethrough;
- wherein the circuitous body comprises segments linked by living hinges that plastically deform in the transition from the first configuration to the second configuration;
- a locking mechanism on adjacent living hinge segments for locking the device in the closed position comprising male and female compressive snap fittings;
- proximal and distal ends oppositely disposed along a lateral axis of the circuitous body; and advancing the distal end of the shaft toward an implantation site such that the luminal axis of the circuitous body of the implant is generally parallel with a bone surface at an implantation site;

rotating the cannula by about 90 degrees such that the luminal axis is generally perpendicular to the bone surface;

translating the shaft proximally relative to the cannula to transition the minimally invasive vertebral implant from the first configuration to a second configuration, wherein in the first configuration the proximal and distal ends are at a maximum separation and in the second configuration the proximal and distal ends are closer together than in the first configuration; and detaching the implantation tool from the minimally invasive vertebral implant.

32. The method for implantation of claim 31, further comprising:
connecting a funnel to a proximal end of the cannula; and
forcing bone graft material through the funnel into an interior volume of the minimally invasive vertebral implant in the second configuration.

33. The method for implantation of claim 31, wherein the implantation site is an intervertebral disc space and includes the following steps prior to the attaching step:
accessing the intervertebral disc space;
distracting adjacent vertebrae on either side of the intervertebral disc space; and
preparing the intervertebral disc space.

34. The method for implantation of claim 31, wherein the circuitous body comprises a rigid biologically inert material selected from the group consisting of: titanium, titanium alloy, and polyetheretherketone.

* * * * *